United States Patent [19]
Brastad

[11] 4,159,018
[45] Jun. 26, 1979

[54] CARDIAC SIGNAL TRANSMITTER UNIT

[75] Inventor: Brian A. Brastad, Wayzata, Minn.

[73] Assignee: Medtronic, Inc., Minneapolis, Minn.

[21] Appl. No.: 883,265

[22] Filed: Mar. 3, 1978

[51] Int. Cl.² ............................................. A61B 5/04
[52] U.S. Cl. ................................. 128/697; 128/904
[58] Field of Search ................. 128/2.06 R, 2.06 B, 128/2.06 E, 2.1 A, 419 PT

[56] References Cited
U.S. PATENT DOCUMENTS

| | | | |
|---|---|---|---|
| 3,029,808 | 4/1962 | Kagan | 128/2.06 B |
| 3,426,150 | 2/1969 | Tygart | 128/2.1 A |
| 3,450,133 | 6/1969 | Birch, Jr. | 128/2.06 E |
| 3,565,058 | 2/1971 | Mansfield | 128/2.06 R |
| 3,768,017 | 10/1973 | Dillman et al. | 128/2.1 A |
| 3,923,041 | 12/1975 | Stasz et al. | 128/2.1 A |

*Primary Examiner*—William E. Kamm
*Attorney, Agent, or Firm*—Cameron, Kerkam, Sutton, Stowell & Stowell

[57] ABSTRACT

A cardiac signal transmitter unit adapted for use by the pacemaker patient which detects and processes electrocardiogram and pacemaker information, and which generates a corresponding audible signal for transmission to a remote location for reception and analysis. The unit employs a three input electrode array for developing a differential signal, has separate channels for processing the electrocardiogram data and the pacemaker data, and includes a fail-safe battery monitor circuit for completely disabling the unit as the battery nears the end of its useful life.

16 Claims, 3 Drawing Figures

CARDIAC SIGNAL TRANSMITTER UNIT

BACKGROUND OF THE INVENTION

1. Field of the Invention

The present invention relates to the field of medical instrumentation and more specifically to portable apparatus for monitoring cardiac signals for transmission to remote locations.

More particularly, this invention describes a battery operated cardiac signal transmitting apparatus adapted for use by the pacemaker patient which detects both electrocardigram pulses (hereinafter EKG pulses or signals) and electrical stimulus pulses produced by the pacemaker (hereinafter artifact pulses or signals), and efficiently converts them into corresponding acoustic signals for transmission to remote locations such as a physician's office or clinic for analysis.

2. Description of the Prior Art

The use of cardiac pacers to sustain life in heart disease cases is well known. It is also well known that cardiac pacers provide an electrical stimulation to the heart and that when the heart beats normally, or in response to an electrical stimulation pulse, it provides an electrical waveform called an EKG pulse. In the prior art, various means of sensing and recording both the pacer artifact pulses and the EKG pulses have been available. It has also been found advantageous to provide equipment which makes the information concerning this sensed artifact and EKG pulses available to the patient, and to transmit such information to a remote station such as a doctor's office, for example by a telephone system. One example of a telephone transmission system is U.S. Pat. Application Ser. No. 235,252, filed Mar. 16, 1972, abandoned for Application Ser. No. 401,648, filed Sept. 28, 1973 and now U.S. Pat. No. 920,005, entitled "EVALUATION SYSTEM FOR CARDIAC STIMULATORS", and assigned to the Assignee of this invention.

U.S. Pat. No. 3,923,041 to Stasz, et al, assigned to the same Assignee as the instant application, also discloses apparatus for detecting cardiac signals and for transmission of the signals to a remote location. The referenced patent further teaches the use of circuitry for providing a quantitative measure of the artifact pulse repetition rate. More precisely, Stasz, et al discloses a dual channel cardiac signal transmitter producing an acoustic output wherein each artifact pulse received and processed is applied to comparator circuitry configured to generate a time gate, which occurs at a predetermined delayed time, within which each subsequent artifact pulse must occur. Thus, any change in the repetition rate of the artifact pulses, due for example to partial depletion of the implanted battery, is detected.

U.S. Pat. No. 3,885,522 to Kennedy, discloses a system for monitoring various cardiac signal parameters and teaches the organization of an apparatus wherein substantially all of the complex signal processing and analysis is accomplished in the unit which is directly coupled to the patient.

While the monitoring and analysis devices available to the pacemaker patient, and/or the patient with heart impairment of some kind, present valuable techniques for providing close follow up monitoring of the patient by the physician, most are sufficiently complex as to make them unavailable as highly portable and fully patient operable moitoring means.

In the prior art, monitoring and analysis devices are available that are powered by self-contained sources such as a battery and include monitoring circuits for detecting the voltage level output of the battery. Such devices detect the patient's cardiac or EKG signals, as well as the artifact pulses as generated by the patient's artificial heart pacemaker. These detected signals are amplified to drive an acoustical transducer in the form of a speaker, which is coupled to the receiver of a normal telephone, whereby such signals are conveyed via common telephone lines to the doctor's office. A problem with such known units is the relatively low drive capability in terms of power applied to its speaker. In the prior art, the signals to be transmitted are applied to a voltage controlled oscillator (VCO), the frequency of whose output varies as a function of the amplitude of the detected input signals. The VCO output is applied via a pair of amplifying transistors directly across the coils of the speaker to ground. Such an arrangement limits the power that may be applied to the speaker; in particular, the power output of the VCO is relatively limited thereby reducing the power to be applied to the speaker. As a result, the quality of the signal transmitted via the telephone lines suffers in terms of its signal to noise ratio. This problem is further complicated by the fact that the sensing device is energized by a battery, whose voltage level decreases with use and time. Thus, as the battery is progressively used, the voltage level and thus the power applied to the speaker becomes attentuated with the result of the quality of the transmitted signal decreases. Thus, the signal received and processed at the doctor's office will eventually become of such quality as to be unintelligible. Though such devices include monitoring circuits sensing the battery voltage to defeat the VCO and further, the VCO circuits are designed to apply a regulated output, there still exists the basic problem of supplying sufficient power to drive the output speaker.

SUMMARY OF THE INVENTION

It is therefore a primary object of this invention to provide improved apparatus for monitoring cardiac signals of patients.

A further object of the present invention is to provide a simple, portable cardiac signal transmitter unit having an acoustic output for use in conjunction with a narrow band transmission medium, such as a telephone line, whereby the transmitted cardiac signal may be received and analyzed at a remote location.

A further object of the present invention is to provide a cardiac signal transmitter unit whereby the patient himself may apply the transmitter unit at any convenient time and place.

Another object of the present invention is to provide a cardiac signal transmitter unit which requires no complex initial calibration or set up by the patient and which may readily be utilized by the non-technical patient, but which still provides a very high degree of validity of the transmitted data.

Another object of the present invention is to provide a cardiac signal transmitter unit having a fail safe battery monitor circuit which will disable the transmitter unit as the battery ages to a point which may cause spurious data transmission.

It is a more specific object of this invention to provide a cardiac signal transmitter having an output driver circuit for efficiently energizing the acoustical transducer, whereby a relatively high level of acoustical energy is applied to the telephone set and via the telephone line to a remote station, e.g., within the physician's office.

It is a still further object of this invention to provide an output driver circuit for a speaker, for efficiently applying the voltage output in a manner to efficiently drive the speaker.

In accordance with these and other objects of the invention, there is disclosed an apparatus for providing acoustical tones manifesting applied electrocardiac signals, to be transmitted over telephone lines, comprising a circuit responsive to a patient's cardiac activity for providing a frequency modulated signal indicative thereof, an acoustical transducer, and a reference switching circuit for driving the transducer in response to the frequency modulated signal.

In an illustrative embodiment of this invention, the apparatus comprises a cardiac signal transmission unit for sensing a patient's electrocardiac signal and the stimulating or artifact pulses as applied by an artificial pacemaker to the patient's heart and for driving an acoustical transducer in an efficient manner, comprising an electrode assembly for connection to the patient's body to develop signals related to the patient's electrocardiac activity and to sense the signals provided by the patient's artificial pacemaker, a voltage controlled oscillator (VCO) responsive to the amplitude of the aforementioned signals for providing an output signal whose frequency is dependent thereon, a self-contained power source for energizing the transmission unit, and an output driver circuit connected across said self-contained power source and including means for establishing a reference level voltage and switching means responsive to the output of the VCO for applying the reference voltage across the acoustical transducer, the reference level means being connected directly across the self-contained power source.

In a further feature of this invention, there is included monitoring means coupled to the power source and to the VCO to disable the VCO when the self-contained power source has expended a predetermined portion of its useful life. The predetermined portion is determined to be sufficient to maintain the reference level voltage established by the reference level means when the VCO is operative.

BRIEF DESCRIPTION OF THE DRAWINGS

Additional objects and advantages of the invention will become apparent to those skilled in the art as the description proceeds with reference to the accompanying drawings, wherein.

DETAILED DESCRIPTION OF THE PREFERRED EMBODIMENT

Figure 1:
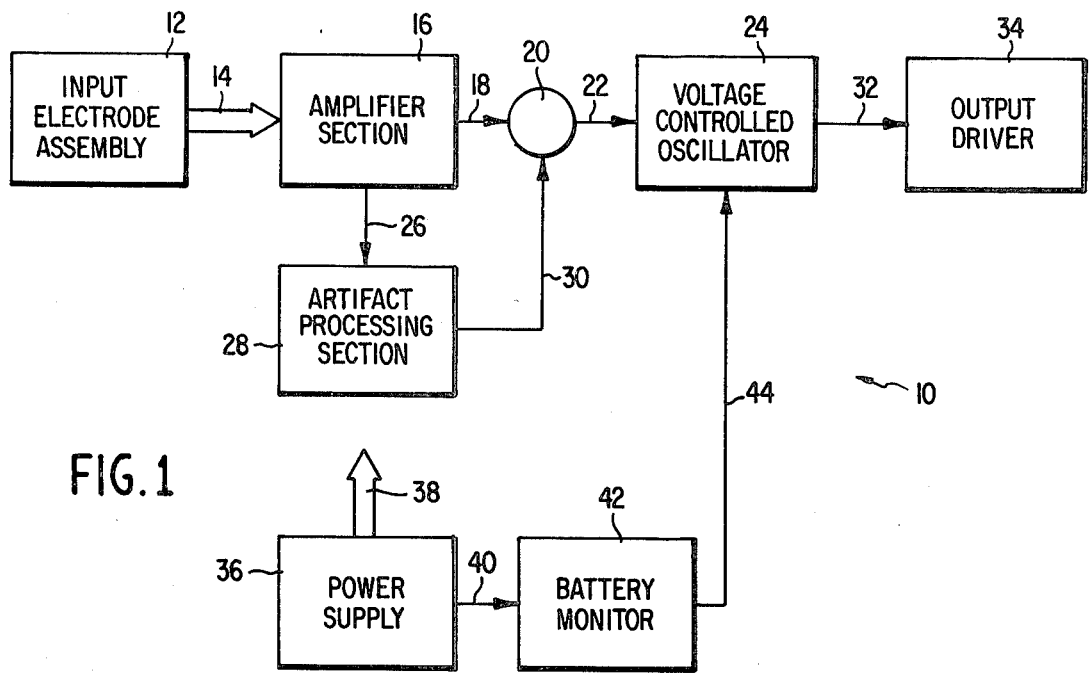
FIG. 1 is a simplified block diagram of the cardiac signal transmitter unit according to the present invention.

Referring first to FIG. 1, there is shown a simplified block diagram of the dual channel cardiac signal transmitter unit of the present invention. The overall transmitter unit 10 has an input electrode assembly 12 coupled by means of a plurality of lines 14 to an AC amplifier section 16. A first output of amplifier section 16 is routed via a line 18 to a first input of a summing circuit 20, whose output is routed via a line 22 to a voltage controlled oscillator (VCO) 24. A second output of amplifier section 16 is routed via a line 26 to an artifact processing section 28, whose output is routed via a line 30 to a second input of the summing circuit 20. The VCO 24 has its output routed via a line 32 to an output driver 34. A power supply 36 provides the required voltages to all sections of the cardiac signal transmitter unit 10 via plurality of lines 38 (shown in simplified form) and provides an input to a battery monitor 42 via a line 40. An output from the battery monitor 42 is routed via a line 44 as an additional input to the VCO 24.

An overview of the functioning of the cardiac signal transmitter unit 10 is facilitated with continued reference to FIG. 1. Briefly, in actual use, the input electrode assembly 12 is attached to several fingers of a patient thereby providing signal voltages representative of physiological phenomena of interest. These signals comprise at least conventional EKG signal and, if applicable, a signal corresponding to a pacemaker artifact pulse. The amplifier section 16 amplifies the desired signals and passes them along to the VCO 24 which produces a carrier frequency in the audio range which is frequency modulated in response to the amplitude of the desired signals. The output driver 34 provides power amplification of the frequency modulated audio signals and also produces an audible output corresponding to the cardiac phenomena being processed. A further output from the amplifier section 16 is used to feed the artifact processing section 28 which separates out the artifact pulse and applies this as an additive input to the VCO 24. Hence, the frequency modulated output applied to the output section 34 is a composite signal containing EKG pulse data and artifact pulse data. The self-contained power supply 36 provides the required voltages to all portions of the cardiac signal transmitter unit 10 and also provides an output to the battery monitor unit 42 which constantly monitors the battery terminal voltage. The battery monitor 42 is configured to disable the VCO 24, when a predetermined end of battery life condition is sensed. In summary, the cardiac signal transmitter unit 10 senses cardiac activity related signals, processes them, and produces an audible output signal corresponding to the cardiac signals. The audible output signal may then be transmitted via existing narrow band lines, such as telephone lines, with a high degree of fidelity and validity to remote locations for reception, demodulation, and analysis.

Figure 2:
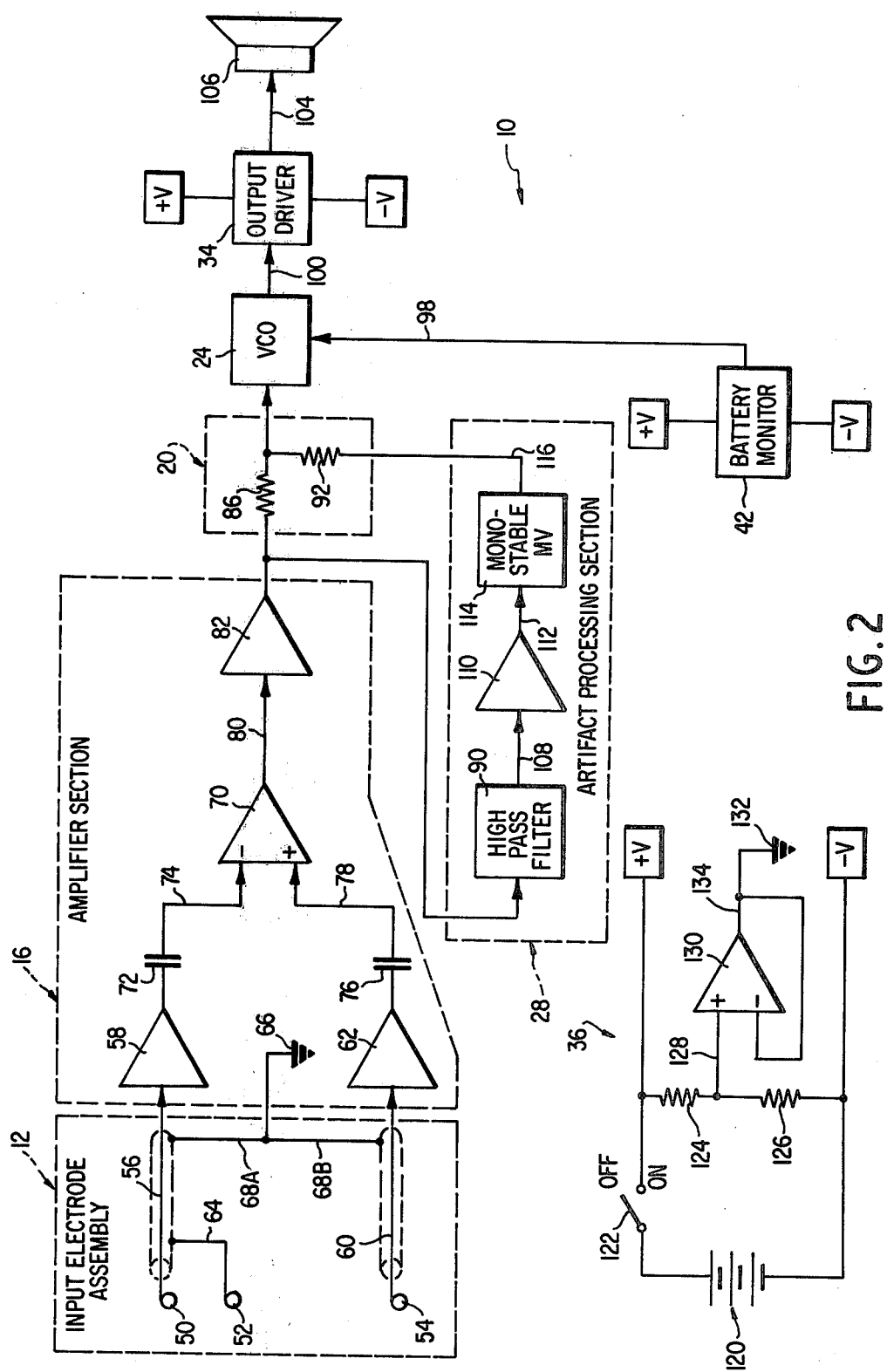
FIG. 2 is a detailed block diagram of the cardiac signal transmitter unit.

Referring now to FIG. 2, there is shown a detailed block diagram of the cardiac signal transmitter unit 10 according to the present invention. The transmitter unit 10 includes the input electrode assembly 12 comprising three electrodes which are configured to provide a differential composite EKG signal voltage via primary electrodes 50 and 54 as referenced to an indifferent (common) electrode 52, to the amplifier section 16. Each of the electrodes is of the finger ring type and may be made of conductive velcro or the like. The first primary electrode 50 is routed via a shielded lead 56 to the amplifier section 16 and in particular, to the input of the first, unity gain, high input impedance amplifier 58; and the second primary electrode 54 is routed via a shielded lead 60 to the input of a second unity gain, high input impedance amplifier 62. The indifferent electrode 52 is connected via a line 64 to the shield of the lead 56. Both shields are further routed to a system ground 66 via a pair of leads 68A and 68B. The output of amplifier 58 is routed to an inverting input node of a differential amplifier 70 via a DC blocking capacitor 72 and a line 74; and the output of amplifier 62 is routed to a non-inverting input node of the differential amplifier 70 via a DC blocking capacitor 76 and a line 78. The differential amplifier 70 accepts the balanced input on its two input nodes and delivers a single ended output via a line 80 to the input of an amplifier 82. The output of amplifier 82 is first routed via a line 84A and a resistor 86 of the summing circuit 20, and is further routed via a line 84B to the input of a high-pass filter 90. The summing circuit 20 includes the resistor 86 and resistor 92 tied to a common point. Resistors 86 and 92 establish the relative magnitudes of two signals which are applied to the control input of a voltage controlled oscillator (VCO) 24 via the summing circuit 20. A second input to the VCO 24 is applied from the battery monitor circuit 42 via a line 98. An output of VCO 24 is routed via a line 100 to an input of high-efficiency output driver 34, and thereafter via line 104 to an output speaker 106.

The artifact processing circuit 28 illustratively includes a high-pass filter 90, an amplifier 110 and a monostable multivibrator 114. More specifically, the output of the high-pass filter 90 is routed via a line 108 to an input of the AC amplifier 110, and thereafter via a line 112 to an input of the monostable multivibrator 114. An output of the monostable multivibrator 114 is routed via a line 116 to the resistor 92 previously mentioned. Thus, it is seen that the two signals applied to the control input of the VCO 24 are processed in a first-channel comprising amplifiers 58, 62, 70 and 82, as well as the summing resistor 86; and in a second channel comprising the gain elements of the first channel plus the elements 90, 110, 114, and the summing resistor 92.

The battery power supply unit 36 is used to provide all of the voltages required in the transmitter unit 10. A battery 120 has its positive terminal routed to a movable pole of a single-pole-single-throw on/off switch 122. The normally open contact (the ON position) of the switch 122 is routed to a first end of a resistor 124, and further to an output terminal designated +V. The negative terminal of battery 120 is routed to a first end of a resistor 126 and further to an output terminal designated −V. The other ends of resistors 124 and 126 are connected together, and are routed via a line 128 to a non-inverting input of an amplifier 130. Amplifier 130 has its inverting input and its output connected directly to a system ground 132 via a line 134. By virtue of the particular configuration of the power supply unit 36, a single conventional two-terminal battery is made to provide both positive and negative DC voltages, each of which is referenced to system ground for use by the remainder of the circuitry. The battery monitor 42 continuously monitors the magnitude of battery 120 terminal voltage and produces at its output, on line 98, a disabling voltage to the VCO 24 when the sensed terminal voltage drops below a predetermined value.

Figure 3:
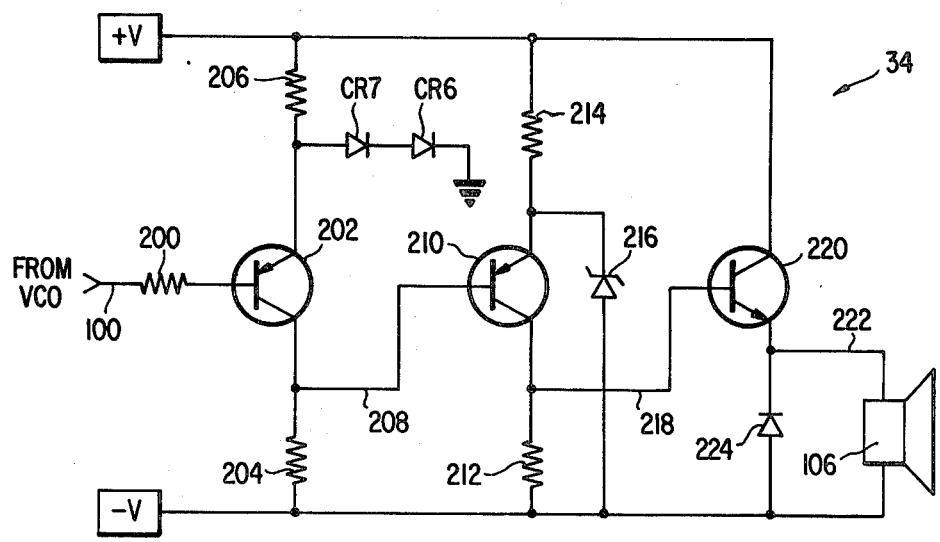
FIG. 3 is a schematic of the high efficiency output circuit for the cardiac signal transmitter unit.

Referring now to FIG. 3, there is shown a schematic diagram of the high-efficiency output driver circuit 34. Briefly, the output driver 34 receives the output of the VCO 24, which contains a constant amplitude, frequency modulated signal in the audio range carrying both analog EKG data and pacemaker artifact data, and provides a power level conversion of this signal suitable to drive the output device. The output signal from the VCO 34 is applied via the line 100 and a series resistor 200 to the base of a level shifting PNP transistor 202 which has its collector returned to the −V bus via a resistor 204, and its emitter returned to the +V bus via a resistor 206. The point of interconnection between the emitter of the transistor 202 and the resistor 206 is connected via series connected diodes CR7 and CR6 to ground. The collector of transistor 202 is further routed via a line 208 to the base of a switching PNP transistor 210, which has its collector returned to the −V bus via a resistor 212 and its emitter returned to the +V bus via a resistor 214. The emitter of transistor 210 is further routed to the cathode of a zener diode 216, whose anode is directly connected to the −V bus. The collector of transistor 210 is routed via a line 218 to the base of an emitter follower connected NPN transistor 220 which has its collector returned directly to the +V bus and its emitter returned via a line 222 to one side of the speaker 106. The other side of the speaker 106 is connected directly to the −V bus, and an inverse diode 224 is connected in parallel with the speaker 106 such that the anode of the diode 224 is connected to the −V bus.

Referring now to FIG. 2 in actual operation, the three input electrodes 50, 52 and 54 are firmly pushed onto the fingers of the patient. Two of the finger ring electrodes (50 and 52) are placed on the fingers of one hand to form respectively an active electrode and an indifferent (common mode) electrode. The other electrode 54, an active electrode, is placed on the fingers of the other hand. The differential signal from the electrodes 50, 52 and 54 is first buffered by the high-input impedance, unity gain input follower amplifiers 58 and 62. Amplifiers 58 and 62 (as well as amplifiers 70, 82, 110 and 130) may be of the large scale integrated circuit types such as are commercially available as CMOS LM 146, or the like. The signal at this point, is a composite of EKG pulses and pacemaker artifact pulses which are typically in the millivolt range. The differential outputs from amplifiers 58 and 62 are routed via the DC blocking capacitors 72 and 76 respectively to the inverting and non-inverting inputs of differential amplifier 70. Capacitors 72 and 76 serve to block the DC offset voltages often encountered on input electrodes, which offset voltages may sometimes reach several hundred millivolts. Amplifiers 70 an 82 provide single ended voltage amplification of the input signal on the order of 40db at the output of amplifier 82, which output is substantially free of common mode signal contamination. The output from amplifier 82 is fed to the resistor 86 of the summing circuit 20 where artifact information is added via the resistor 92, and the composite signal is then fed to the control input of the VCO 24.

The independent channel (the artifact processing section 28, of FIG. 1) for processing the pacemaker artifact comprises the serial arrangement of the high-pass filter 90, the AC amplifier 110 and the monostable multivibrator 114. The filter 90, as supplied from the amplifier 82 via the line 84B, readily passes the high-frequency components of the artifact pulses and effectively blocks the lower frequency EKG pulses. These artifact pulses are typically of order 300 $\mu$s to 2 ms in duration with fairly steep rise and fall times. The output pulses from the high-pass filter are amplified by the AC amplifier 110 having an illustrative gain in the order of 45 and are used to trigger the monostable multivibrator 114 such that a single pulse of fixed amplitude and duration is produced for each artifact pulse processed. The monostable multivibrator 114 has a threshold level (e.g. of 0.7 v) which is exceeded only upon the appearance of an artifact signal, thus actuating the multivibrator 114. The monostable multivibrator 114 output pulsewidth is preset to be on the order of 10 ms, to permit a fixed number of cycles (e.g. 20) of the carrier signal to be transmitted over the telephone line so as to be accurately detected at the receiver. The pulse is summed via the resistor 92 such that the control input of VCO 24 consists of an analog voltage representative of EKG data, and a single pulse of fixed amplitude and duration representative of each artifact pulse detected.

The VCO 24 consists of an astable multivibrator having a predetermined rest frequency, whose output frequency is linearly controlled by the composite waveform applied to its control input by the summing circuit 20, and which may further be completely disabled by a control voltage applied from the battery monitor 96 via the line 98. In normal operation, the VCO 94 produces a symmetrical square wave rest frequency, illustratively 1500 Hz, which several tens of hertz per millivolt of differential signal developed at the input electrodes. The VCO 24 output frequency is further shifted abruptly to 2100 Hz on the occurrence of the 10 ms output of the multivibrator 114. This frequency modulated square wave, in the mid-audio range, is then routed to the output driver 34 and the speaker 106 for conversion into an acoustic output.

The power supply unit 36 shown in FIG. 2 is configured to provide equal positive (+V) and negative (−V) voltages both referenced to system ground from a conventional two-terminal, commercially available battery 120. The dual polarity sources are required for proper operation of the operational amplifiers as used throughout the transmitter unit 10. The battery 120 is paralleled by a series connection of the two equal resistors 124 and 126 whose common connection is applied to the non-inverting input of the voltage follower amplifier 130. Conventionally, the voltage follower action of amplifier 130 provides an electronic ground, causing the output on line 134 to follow the input applied via the line 128 to the non-inverting input. As the output on line 134 is strapped to a reference point designated system ground, the non-inverting input is constrained to remain at this same potential. This voltage follower follower action in turn assures that the +V and −V terminals will always be equal in magnitude as the battery ages. This particular configuration of the power supply 118 greatly stabilizes the long-term DC operation of the transmitter unit 10, and attenuates noise that is imposed on the unit 10 via the input electrode assembly 12.

The battery monitor 42 serves to continuously monitor the terminal voltage of the battery 120 and to produce the control voltage on line 98 which either enables or disables the VCO 24. The battery monitor 96 performs a conventional comparison of a portion of the battery terminal voltage against an internal voltage reference source and provides an abrupt shift in its enabling control voltage when its internal comparator senses that the battery terminal voltage has decreased to some predetermined fraction of the rated volated of a fresh battery, e.g. six volts for a nine-volt battery 120. The line 98 is shown as being applied to a second input of the VCO 124, but functionally the control voltage may also be applied to the summing point 88 as an additional two-valued input to the frequency controlling input terminal. In this latter case, the two-valued control voltage would be established so as to merely enable normal operation (as described above) of the VCO 24 when the battery monitor 42 comparator determines that the battery terminal voltage is above the predetermined value, or to completely preclude oscillations of the VCO 24 when the battery monitor 42 comparator determines that the predetermined end of life voltage has been reached.

The output of the VCO 24 is applied via conductor 100 to the output driver 34, as seen in FIGS. 2 and 3. The output of the VCO 24 is indicative of the EKG data and the artifact pulses of the artificial pacemaker; in particular the EKG data causes the VCO 24 to vary its output about a frequency in the order of 1500 Hz. Upon the appearance of an artifact pulse, the monostable multivibrator 114 is triggered or actuated to apply a 10 ms actuating pulse to the VCO 24, to energize it to generate a signal of a substantially fixed frequency in the order of 2100 Hz for a corresponding period. The voltage output from the VCO 24 remains substantially constant in the order of +1.5 to −1.5 volts and is tied to circuit ground. As shown in detail in FIG. 3, the VCO output is applied via a conductor 100 and a resistor 200 to the base of the PNP transistor 202 which serves as an input level shifter and which is configured as a common emitter stage. In other words, the base of the transistor 202 presents a high input impedance, and the output as derived from its collector presents a low impedance and is DC coupled directly to the base of the PNP transistor 210.

In operation, as the output of the VCO 24 goes high, the transistor 202 is rendered non-conductive and when the VCO output goes low, the transistor 202 is rendered conductive. As indicated in FIGS. 2 and 3, the voltage drive from the power source 36 is applied across the resistor 206, the transistor 202 and the resistor 204. The point of interconnection beteen the resistor 206 and the emitter of transistor 202, is established at a reference potential in the order of 1.5 volts due to the presence of the diodes CR7 and CR6. Upon being rendered conductive, substantially most of the reference level potential (1.5 volts) is applied from the collector of the transistor 202 to the base of the PNP transistor 210, also configured as a common emitter stage. When transistor 202 is rendered conductive, the increased potential applied to the base of the transistor 210 renders it non-conductive. As seen in FIG. 3, the reference potential is established by the zener diode 216; illustratively, this potential is in the order of 3.8 volts. The output from the collector of the transistor 210 is DC coupled directly to the base of the NPN transistor 220, which serves as an emitter-follower power stage driving the speaker 106. Thus when the transistor 210 is rendered conductive, substantially the entire reference potential is applied via conductor 218 to the base of the transistor 220 rendering it conductive to supply a potential equal to the reference potential less the voltage drop across the base-to-emitter junction of the transistor 220, to provide a driving voltage to the speaker 106. Thus, a substantial portion of the potential developed by the power source 34 and in particular the battery 120 is applied across the speaker 106, in contrast with only applying the voltage ouptut of the VCO.

In this regard, the voltage and thus the power applied to drive the speaker 106 is maintained relatively constant by the zener diode 216. Thus, as the energy of the battery 120 falls in use, the power driving the speaker 106 and thus its acoustical output will remain relatively constant until the battery monitor 42 senses a decrease in the voltage level of the battery 120, to disable the VCO 24, as described above. In this regard, the reference voltage established by the zener diode 216 is set to be less than that critical voltage, below which the battery monitor 42 will disable the VCO 24. Thus, as long as the battery 120 is sensed to be in its operative range, sufficient potential will be applied across the zener diode 216 to maintain it operative at the reference or fixed potential. Further, as an observation of FIGS. 2 and 3 indicates, the battery 120 is essentially applied across the speaker 106, as opposed to connecting the battery across the speaker to ground, thus preventing the relatively large current flowing in the speaker 106 from flowing through the ground network, which could cause serious interference with the ability of the input circuit to sense the small (millivolt) signals on the electrodes.

In this manner, the speaker 106 is driven in an efficient manner to allow acoustic coupling to the mouthpiece of a conventional telephone handset at a level which assures an optimum, nondistorting telephone transmission from the patient's location to the receiving equipment remotely located at the physician's office or clinic.

Although the invention has been described in terms of a preferred embodiment, the invention should not be deemed limited thereto, since other embodiments and modifications will readily occur to one skilled in the art. It is therefore to be understood that the appended claims are intended to cover all such modifications and changes as fall within the true spirit and scope of the invention.

What is claimed is:

1. A cardiac signal transmission unit adapted to be operated from a self-contained power source, said transmission unit comprising:
   (a) input electrode means adapted to be connected to a patient's body for developing differential signals corresponding to the patient's cardiac-related activities;
   (b) amplifier means connected to said input electrode means for providing amplified signals corresponding to the differential signals;
   (c) a voltage controlled oscillator (VCO) coupled to said amplifier means for providing output signals of a frequency corresponding to the amplitude of the amplified signal;
   (d) acoustical transducer means for providing an acoustical output; and
   (e) driver means comprising reference means adapted to be coupled directly across said self-contained power source for providing a relatively constant, reference level voltage, and switch means responsive to the output of said VCO for connecting the reference level voltage directly across the inputs of said acoustical transducer and for driving said acoustical transducer means with the relatively constant level voltage.

2. The cardiac signal transmission unit as claimed in claim 1, wherein there is included monitoring means connected to said power source and responsive to the output of said power source below a predetermined level for disabling said VCO.

3. The cardiac signal transmission unit as claimed in claim 2, wherein the predetermined level at which said VCO is disabled is selected to prevent said reference means from providing unregulated reference level voltage to said acoustical transducer means.

4. The cardiac signal transmission unit as claimed in claim 3, wherein said reference means comprises a zener diode, and said monitoring means determines the predetermined level, whereby when the output of said self-contained power source decreases below the predetermined level, said VCO is disabled.

5. A dual channel cardiac signal transmission unit having a self-contained power source and adapted to be connected to a body for producing acoustic signals corresponding to EKG signals and pacemaker artifact signals, said unit comprising:
   (a) three input electrodes for connection to the body to provide differential signals corresponding to cardiac activity including at least EKG signals and artifact signals;
   (b) a first electronic channel for amplifying said differential signals and for providing single ended amplified signals corresponding to said EKG and artifact signals:
   (c) a second electronic channel for processing said amplified signals and for providing pulse output signals corresponding only to said artifact signals;
   (d) a voltage controlled oscillator (VCO) connected to said first and second electronic channels for converting said amplified signals and said pulse output signals into corresponding signal frequencies;
   (e) output conversion means connected to said voltage controlled oscillator for converting said signal frequencies into corresponding acoustic signals;
   (f) means for monitoring the output voltage level of said power source to determine when the voltage level has decreased below a predetermined level and for initiating a control signal thereupon;
   (g) means for silencing said acoustic signals by application of said control signal to said VCO thereby disabling said signal frequencies; and
   (h) driver means comprising reference means adapted to be coupled directly across said self-contained power source for providing a relatively constant reference level voltage, and switch means responsive to the output of said VCO for connecting the reference level voltage directly across the inputs of said acoustical transducer to drive said acoustical transducer with the relatively constant reference level voltage, said predetermined level being set to prevent said reference means from deregulating its reference level voltage as the output of said power source decreases.

6. The cardiac signal transmission unit as claimed in claim 5, wherein said reference means comprises a zener diode.

7. The cardiac signal transmission unit as claimed in claim 6, wherein said switch means comprises:
   (a) high-input impedance level shifting means connected to said VCO to process the signal frequencies into shifted level signal frequencies;
   (b) intermediate amplifier means connected to said level shifting means and coupled to said zener diode, for selectively applying the reference level voltage as established by said reference means to an output in response to the shifted level signal; and
   (c) power output means connected to said output of said intermediate amplifier means for increasing the power level of the shifted level signal as applied to said acoustical transducer means.

8. The cardiac signal transmission unit as claimed in claim 5, wherein there is further included means coupled to said self-contained power source for setting the voltages as derived from the outputs of said source to predetermined levels with respect to ground.

9. The cardiac signal transmission unit as recited in claim 5, wherein said first electronic channel comprises a high input impedance amplifier connected to each of a first and second of said input electrodes and a third input electrode is connected so as to provide a reference point for said differential signals.

10. The dual channel cardiac signal transmission unit as recited in claim 9 wherein said second electronic channel comprises a monostable multivibrator for providing said pulse output signals whereby a signal pulse of predetermined constant duration is produced for each artifact signal processed.

11. Apparatus for providing and transmitting together stimulating pulses as applied by an artificial pacemaker to a patient's heart and electro-cardiac signals of the patient's heart over a limited bandwidth medium to a remote station, said apparatus comprising:
 (a) electrode means adapted to be attached to the patient's body for sensing the stimulating pulses and the electro-cardiac signals;
 (b) modulation means for generating a carrier signal of a frequency to be transmitted over the limited bandwidth medium dependent upon the signals developed by said electrode means;
 (c) acoustical transducer means;
 (d) drive means coupled to said modulation means and to the self-contained power source for driving said acoustical transducer means, and comprising reference means for establishing a relatively constant reference level voltage, and switch means responsive to the output of said modulation means for selectively applying the reference level voltage to said acoustical transducer means to drive said acoustical transducer means with the relatively constant reference level voltage.

12. The transmission apparatus as claimed in claim 11, wherein there is included monitoring means connected to said power source for disabling said modulation means when the output level of said power source has decreased below a predetermined level, the predetermined level at which said modulation means is disabled is selected to prevent said reference means from providing unregulated reference level voltage to said acoustical transducer means.

13. Apparatus for providing acoustical tones manifesting applied electrocardiac signals, said tones adapted to being transmitted over telephone lines, said apparatus comprising:
 (a) means for providing a frequency modulated signal in response to said applied cardiac signals;
 (b) acoustical transducer means;
 (c) switchable reference voltage means coupled directly to said acoustical transducer means for driving said transducer means in response to said frequency modulated signal with a relatively constant voltage level signal.

14. Invention according to claim 13, wherein said apparatus further includes battery means and means responsive to said battery means providing a voltage below a certain value for disabling said frequency modulated signal providing means to prevent said switchable reference voltage means from deregulating the relatively constant voltage level signal applied to said acoustical transducer means.

15. The invention according to claim 14, wherein said switchable reference voltage means includes a zener diode coupling in parallel with said battery means, and switchably being connected to drive said transducer means.

16. The invention according to claim 15, wherein said switchable reference voltage means further includes a switching transistor which in response to said frequency modulated signal connects said diode to drive said transducer means.

* * * * *